US009040566B2

(12) United States Patent
Klar et al.

(10) Patent No.: US 9,040,566 B2
(45) Date of Patent: May 26, 2015

(54) ADENOSINE A1 AGONISTS FOR THE TREATMENT OF GLAUCOMA AND OCULAR HYPERTENSION

(75) Inventors: Jürgen Klar, Wuppertal (DE); Georges Von Degenfeld, Leverkusen (DE); Hans-Georg Lerchen, Leverkusen (DE); Barbara Albrecht-Küpper, Wülfrath (DE); Andreas Knorr, Erkrath (DE); Peter Sandner, Wuppertal (DE); Daniel Meibom, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/819,790

(22) PCT Filed: Aug. 29, 2011

(86) PCT No.: PCT/EP2011/064829
§ 371 (c)(1),
(2), (4) Date: Apr. 11, 2013

(87) PCT Pub. No.: WO2012/028585
PCT Pub. Date: Mar. 8, 2012

(65) Prior Publication Data
US 2013/0210797 A1    Aug. 15, 2013

(30) Foreign Application Priority Data

Sep. 2, 2010    (EP) .................................... 10175151

(51) Int. Cl.
| | |
|---|---|
| *A01N 43/40* | (2006.01) |
| *A61K 31/44* | (2006.01) |
| *C07D 409/00* | (2006.01) |
| *C07D 411/00* | (2006.01) |
| *C07D 405/00* | (2006.01) |
| *C07D 417/12* | (2006.01) |
| *A61K 9/00* | (2006.01) |
| *A61K 9/08* | (2006.01) |
| *A61K 31/4439* | (2006.01) |
| *A61K 45/06* | (2006.01) |
| *C07D 413/12* | (2006.01) |
| *C07D 417/14* | (2006.01) |

(52) U.S. Cl.
CPC ............ *C07D 417/12* (2013.01); *A61K 9/0048* (2013.01); *A61K 9/08* (2013.01); *A61K 31/4439* (2013.01); *A61K 45/06* (2013.01); *C07D 413/12* (2013.01); *C07D 417/14* (2013.01)

(58) Field of Classification Search
CPC . A61K 31/381; A61K 31/421; A61K 31/426; C07D 213/89
USPC ......... 514/340, 342; 546/268.7, 269.1, 280.4, 546/283.4
See application file for complete search history.

(56) References Cited

U.S. PATENT DOCUMENTS

| | | | |
|---|---|---|---|
| 4,052,510 | A | 10/1977 | Simpson et al. |
| 5,670,525 | A | 9/1997 | Urbahns et al. |
| 5,889,002 | A | 3/1999 | Nielsen et al. |
| 6,191,280 | B1 | 2/2001 | Hamprecht et al. |
| 6,586,441 | B2 | 7/2003 | Borroni et al. |
| 6,632,823 | B1 | 10/2003 | Vernier et al. |
| 6,693,102 | B2 | 2/2004 | Stasch et al. |
| 6,706,717 | B2 | 3/2004 | Barrish et al. |
| 6,743,798 | B1 | 6/2004 | Straub et al. |
| 6,833,364 | B1 | 12/2004 | Straub et al. |
| 6,864,287 | B1 | 3/2005 | Alonso-Alija et al. |
| 7,045,631 | B2 | 5/2006 | Rosentreter et al. |
| 7,135,486 | B1 | 11/2006 | Rosentreter et al. |
| 7,173,036 | B2 | 2/2007 | Sircar et al. |
| 7,173,037 | B2 | 2/2007 | Alonso-Alija et al. |
| 7,186,716 | B2 | 3/2007 | Wei et al. |
| 7,674,825 | B2 | 3/2010 | Alonso-Alija et al. |
| 7,692,017 | B2 | 4/2010 | Dinsmore et al. |
| 7,705,043 | B2 | 4/2010 | Alonso-Alija et al. |
| 7,709,504 | B2 | 5/2010 | Krahn et al. |
| 7,781,470 | B2 | 8/2010 | Alonso-Alija et al. |
| 7,932,259 | B2 | 4/2011 | Nakazato et al. |
| 7,951,811 | B2 | 5/2011 | Nakazato et al. |
| 8,242,281 | B2 | 8/2012 | Rosentreter et al. |
| 8,304,412 | B2 | 11/2012 | Nell et al. |
| 8,420,825 | B2 | 4/2013 | Vakalopoulos et al. |
| 8,426,602 | B2 | 4/2013 | Meibom et al. |
| 8,440,700 | B2 | 5/2013 | Nell et al. |
| 2003/0232860 | A1 | 12/2003 | Harada et al. |

(Continued)

FOREIGN PATENT DOCUMENTS

| | | |
|---|---|---|
| EP | 0608565 | 12/1993 |
| JP | 09132529 | 5/1997 |

(Continued)

OTHER PUBLICATIONS

National Eye Institute, "Vision Problems in the U.S.: Prevalence of Adult Vision Impairment and Age-Related Eye Disease in America", 2002, National Institutes of Health, pp. 1-6.*
Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.

(Continued)

*Primary Examiner* — Sarah Pihonak
(74) *Attorney, Agent, or Firm* — Karen B. King

(57) ABSTRACT

The present invention relates to the use of selective adenosine A1 agonists, in particular the dicyanopyridines of formula (I), for the treatment and/or prophylaxis of glaucoma and ocular hypertension as well as the their use for the production of a medicament for the treatment and/or prophylaxis of glaucoma and ocular hypertension.

11 Claims, 7 Drawing Sheets

(56) References Cited

U.S. PATENT DOCUMENTS

| | | | |
|---|---|---|---|
| 2004/0176446 A1 | 9/2004 | Alonso-Alija et al. | |
| 2005/0182105 A1 | 8/2005 | Nirschi et al. | |
| 2005/0227972 A1* | 10/2005 | Rosentreter et al. | 514/227.5 |
| 2005/0250774 A1 | 11/2005 | Ono et al. | |
| 2006/0264432 A1 | 11/2006 | Rosentreter et al. | |
| 2007/0066630 A1 | 3/2007 | Palani et al. | |
| 2007/0293670 A1 | 12/2007 | Nakazato et al. | |
| 2008/0167321 A1 | 7/2008 | Kamboj et al. | |
| 2009/0221649 A1 | 9/2009 | Krahn et al. | |
| 2010/0009973 A1 | 1/2010 | Rhodes et al. | |
| 2010/0069363 A1 | 3/2010 | Nell et al. | |
| 2010/0093728 A1 | 4/2010 | Nell et al. | |
| 2011/0136871 A1 | 6/2011 | Hübsch et al. | |
| 2011/0294718 A1* | 12/2011 | Lerchen et al. | 514/1.3 |

FOREIGN PATENT DOCUMENTS

| | | |
|---|---|---|
| JP | 10324687 | 12/1998 |
| JP | 2003183254 | 7/2003 |
| WO | 9534563 | 12/1995 |
| WO | 9727177 | 7/1997 |
| WO | 9903861 | 1/1999 |
| WO | 0248115 | 6/2002 |
| WO | 0250071 | 6/2002 |
| WO | 03091246 | 11/2003 |
| WO | 2004014372 | 2/2004 |
| WO | 2004054505 | 7/2004 |
| WO | 2005007647 | 1/2005 |
| WO | 2008008059 | 1/2008 |
| WO | WO 2009015811 A1 * | 2/2009 |
| WO | WO 2010127210 A1 * | 11/2010 |

OTHER PUBLICATIONS

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible Derivatives for Various Functional Groups and Chemical Entities," Elsevier Science Publishers B.V. 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketones via Mixed Anhydride and Coupling Reagent Methods: A New Approach to the Arndt-Eistert Synthesis," Tetrahedron Letters, 2001, 42: 7099-7102.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyanopyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5- Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ellenbogen et al, "Trial to evaluate the management of paroxysmal superventricular tachycardia during an electrophysiology study with tecadenoson," Circulation, 2005, 111:3202-3208.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using α,β-Unsaturated Nitriles: Facile Synthesis of Pyridine Derivatives," Synthesis Communications, Jul. 1981, pp. 531-533.

Klotz, et al.:"Comparative Pharmacology of Human Adenosine Receptor Subtypescharacterization of Stably Transfected Receptors in CHO Cells," Naunyn-Schmiedeberg's Arch Pharmacol, 1998, 357:1-9.

Klotz:"Adenosine Receptors and their Ligands," Naunyn-Schmiedeberg's Arch. Pharmacol., 2000, 362: 382-391.

Martyn, et al.:"Obesity-induced Insulin Resistance and Hypoglycemia: Etiologic Factors and Molecular Mechanisms," Anesthesiology, 2008, 109:137-148.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

Olah, et al.:"Cloning, Expression, and Characterization of the Unique Bovine A1 Adenosine Receptor," Journal of Biological Chemistry, May 25, 1992, 267(15):10764-10770.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Poulsen, et al.:"Adenosine Receptors: New Opportunities for Future Drugs," Bioorganic & Medicinal Chemistry, Jan. 8, 1998, 6(6): 619-641.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

(56) References Cited

OTHER PUBLICATIONS

Quintela, et al.:"Synthesis, Antihistaminic and Cytotoxic Activity of Pyridothieno- and Pyridodithienotriazines", Eur. J. Med. Chem, 1998, 33:887-897.

Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.

Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.

Ruhe, et al.:"Use of Antioxidant Nutrients in the Prevention and Treatment of Type 2 Diabetes," Journal of the American College of Nutrition, 2001, 20(5): 363S-369S.

Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

Sheridan:"The Most Common Chemical Replacements in Drug-Like Compounds," J Chem. Inf. Comput. Sci., 2002, 42:103-108.

Suttner, et al.:"The Heart in the Elderly Critically Ill Patient," Curr. Opin. Crit. Care, Oct. 2002, 8(5):389-94, abstract retrieved from MEDLINE Accession No. 2002495386, PubMed ID: 12357105.

Szydlowski, et al.:"Biological Role of Chromium," Diabetologia Polska, 2003, 10(3):365-370, English language abstract retrieved from EMBASE Accession No. 2004016455.

Vasudevan A. et al., "Aminopiperidine indazoles as orally efficacious melanin concentrating hormone receptoer-1 antagonists," Bioorg. Med. Chem. Lett. 2005, 15 (23), 5293-5297.

Vippagunta, et al.:"Dystalline Solids," Advanced Drug Delivery Reviews, May 16, 2001, 48(1):3-26.

West:"Solid State Chemistry and its Applications," Wiley, New York, 1988, pp. 358 & 365.

Ye, et al.:Organic Synthesis with $\alpha$-Diazocarbonyl Compounds, Chem. Rev. 1994, 94:1091-1160.

Zhu, G. et al., "Design and synthesis of pyridine-pyrazolopyridine-based inhibitors of protein kinase B/Akt," Bioorg. Med. Chem. 2007, 15 (6), 2441-2452.

Yu, et al:"Physical Characterization of Polymorphic Drugs: An Integrated Characterization Strategy," Pharmaceutical Science & Technology Today, Jun. 1998, 1(3):118-127.

U.S. Appl. No. 13/805,653, filed Dec. 19, 2012.

* cited by examiner

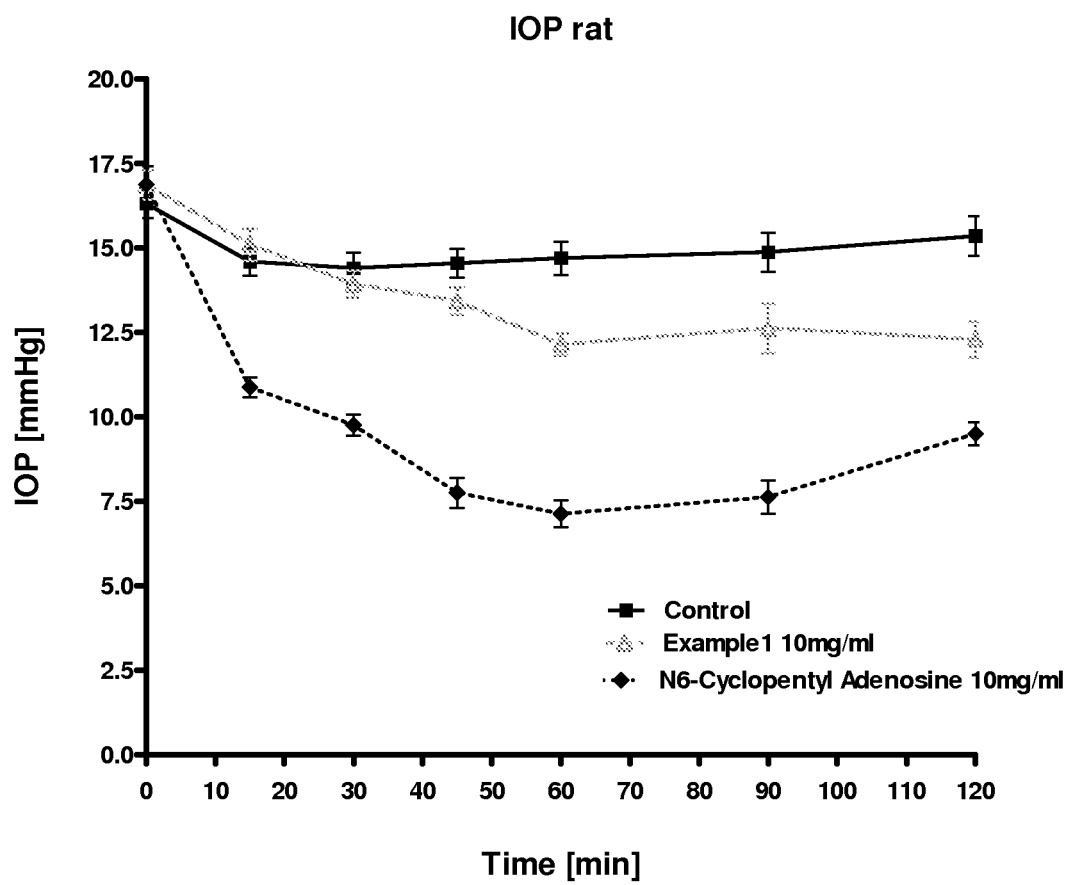
FIG 1A: IOP as mmHg in unconscious rats after topical administration of 10 mg/ml Example 1, 10mg/ml $N^6$-Cyclopentyladenosine and control.

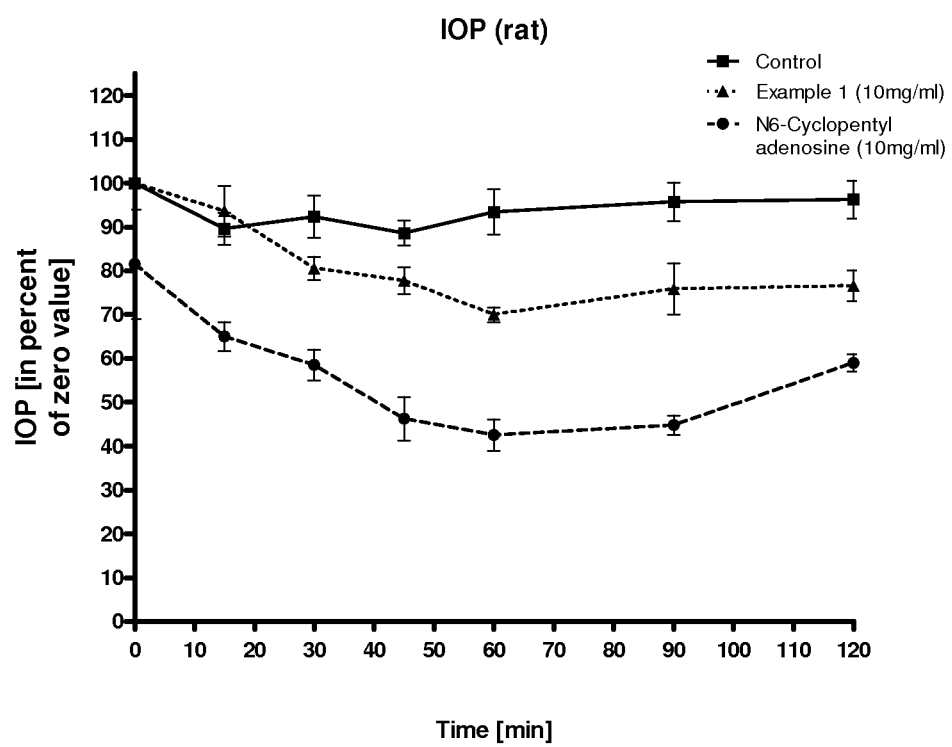
FIG 1B: IOP as percent of zero value in unconscious rats after topical administration of 10 mg/ml Example 1, 10mg/ml $N^6$-Cyclopentyladenosine and control.

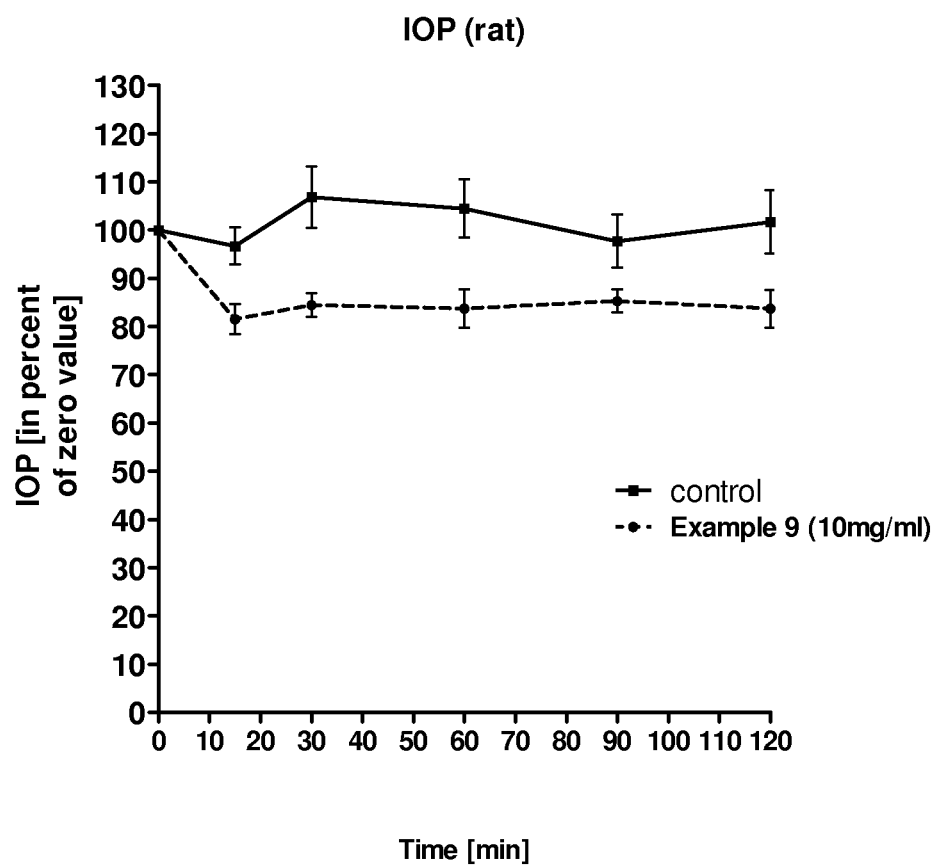
FIG 2: IOP as percent of zero value in unconscious rats, after topical administration of 10 mg/ml Example 9 and control.

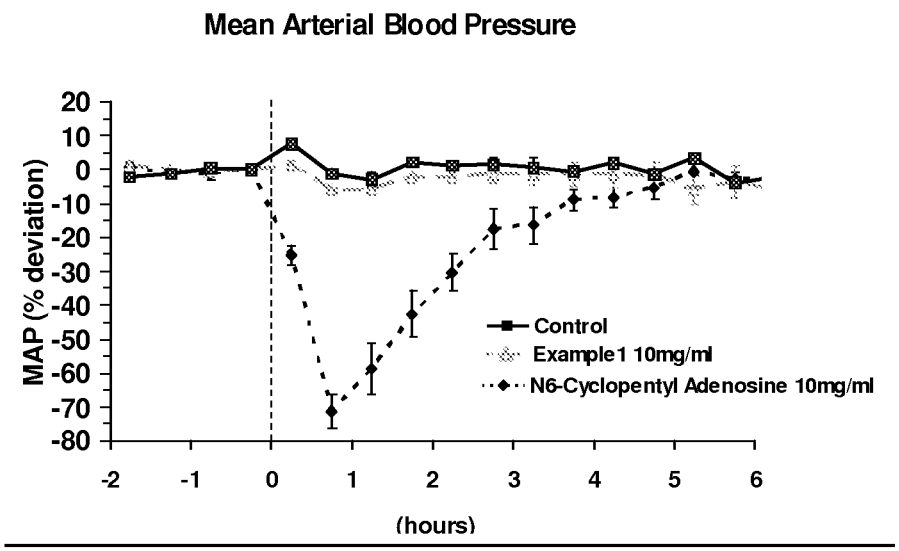
FIG 3: Blood pressure in conscious rats after topical administration of 10mg/ml Example 1 and $N^6$-Cyclopentyladenosine
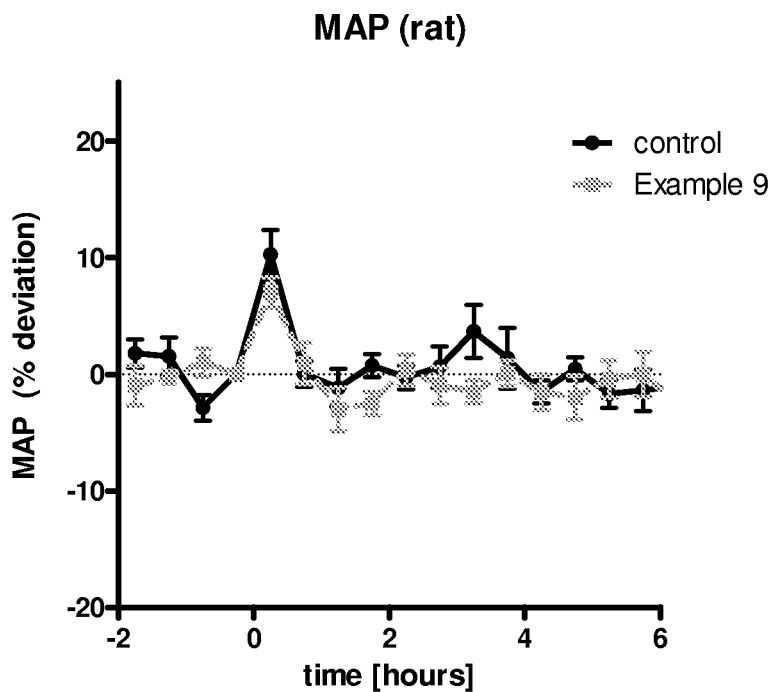
FIG 4: Blood pressure in conscious rats after topical administration of 10mg/ml Example 9 and control.

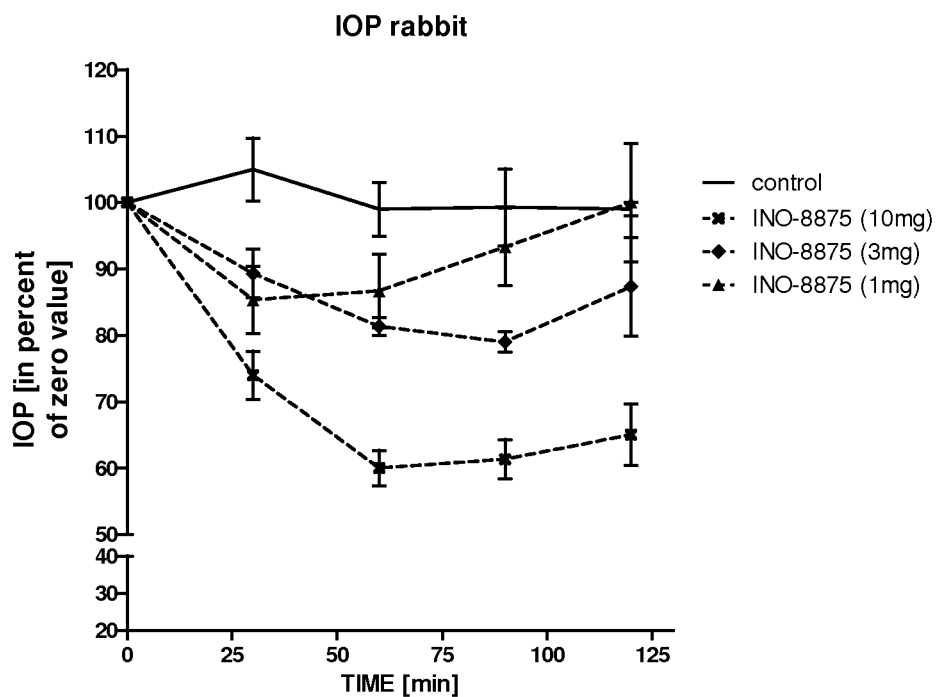
FIG 5: IOP in conscious rabbits after topical administration of INO-8875 and control.
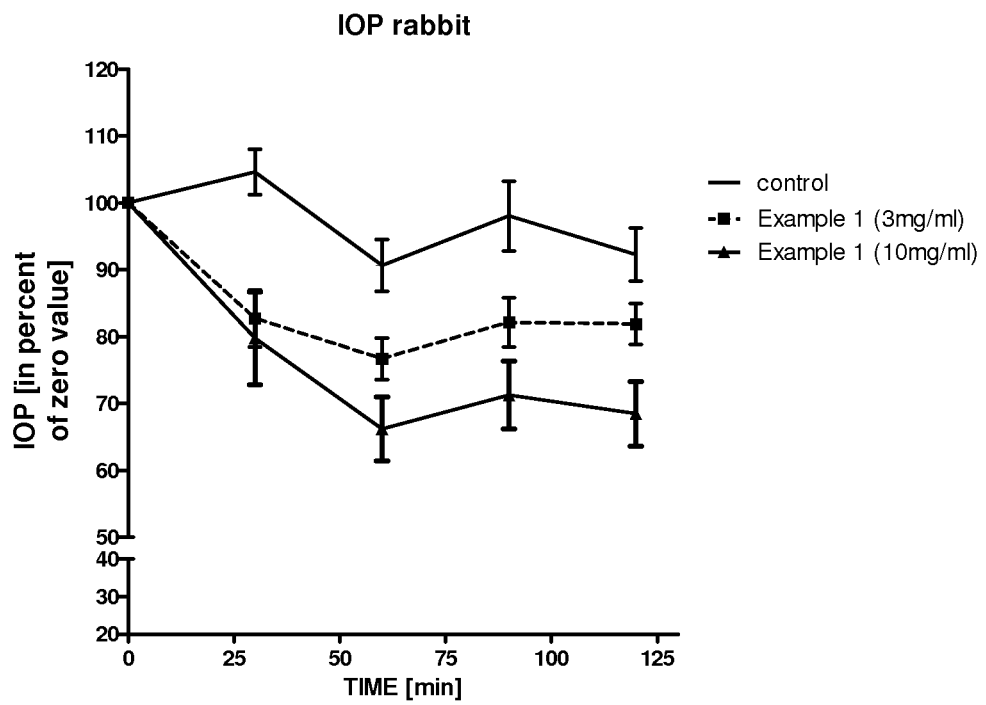
FIG 6: IOP in conscious rabbits after topical administration of Example 1 and control.

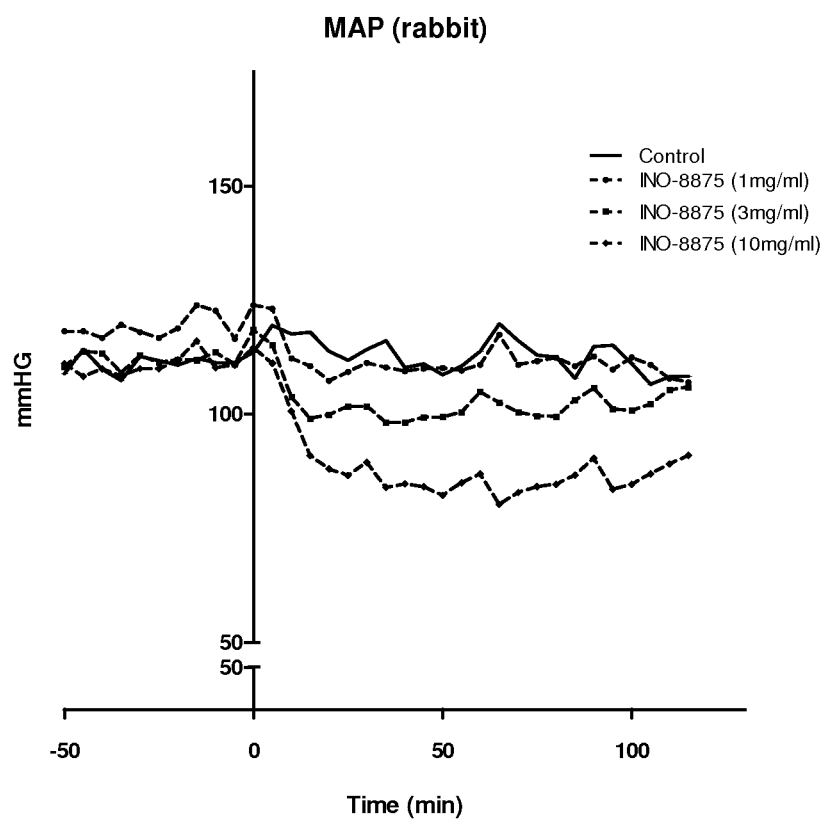
FIG 7: Effects on mean arterial pressure of conscious rabbits after topical administration of INO-8875

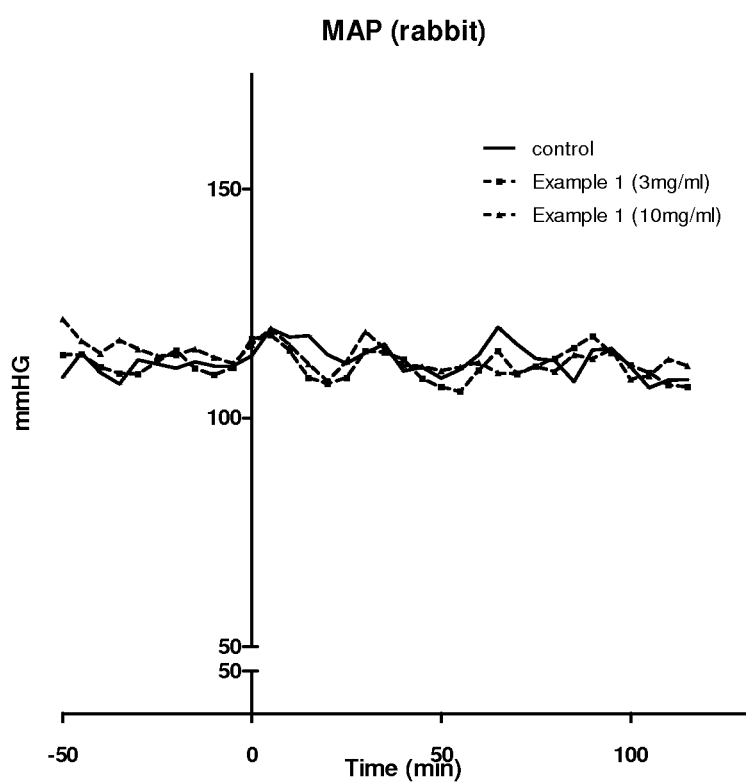
FIG 8: Blood pressure in conscious rabbits after topical administration of Example 1.

ADENOSINE A1 AGONISTS FOR THE TREATMENT OF GLAUCOMA AND OCULAR HYPERTENSION

The present invention relates to selective adenosine A1 agonists, in particular the dicyanopyridines of formula (I), for the use in a method for the treatment and/or prophylaxis of glaucoma, normotensive glaucoma, ocular hypertension and/or combinations thereof as well as the their use for the production of a medicament for the treatment and/or prophylaxis of glaucoma, normotensive glaucoma, ocular hypertension and/or combinations thereof.

BACKGROUND OF THE INTERVENTION

Glaucoma is a degenerative disease comprising a group of debilitating eye diseases that are a leading cause of permanent loss of visual function due to irreversible damage to the optical nerve. Glaucoma refers further to a disease of the eye, characterized and caused by damage of the optic nerve head, degeneration of ocular tissues, and/or elevated intraocular pressure. There are several functionally or morphologically distinct types of glaucoma which in general are accompanied by elevated intraocular pressure (IOP).

The increased IOP is considered to be causally related to the pathological progress of the disease. In patients with ocular hypertension intraocular pressure is elevated but no apparent loss of visual function has occurred. These patients are considered to be at high risk for a potential development of visual loss associated with glaucoma. Some patients which show a glaucomatous vision field loss have a normal to low intraocular pressure. These so called normotension or low tension glaucoma patients can also benefit form agents that decrease intraocular pressure. The loss of visual function and the progressive deterioration associated with glaucoma and ocular hypertension can generally be ameliorated with medications that reduce elevated intraocular hypertension when glaucoma or ocular hypertension is detected early.

Glaucoma—on the basis of its etiology—refers also to primary or secondary glaucoma. Primary glaucoma in adults (congenital glaucoma) may be either open-angle or acute or chronic angle-closure.

Primary glaucoma is characterized by increased intraocular tension which is due to the obstruction of aqueous humor outflow. In chronic open-angle glaucoma (POAG), the anterior chamber and its anatomic structures appear normal, but drainage of the aqueous humor is hampered. In acute or chronic angle-closure, the filtration angle is narrowed, the anterior chamber is shallow and the iris may obstruct the trabecular meshwork at the entrance of the canal of Schlemm Dilation of the pupil may push the root of the iris forward against the angle, and may produce pupilary block and thus precipitate an acute attack. A predisposion to acute angle-closure glaucoma attacks with various degrees of severity is know in patients eyes with narrow anterior chamber angles Secondary glaucoma is characterized and caused by any interference which effects the flow of aqueous humor from the posterior chamber into the anterior chamber and subsequently, into the canal of Schlemm. Also inflammatory disease of the anterior segment may inhibit aqueous outflow by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Several therapies for treating glaucoma or ocular hypertension have been proven to be effective in clinical practice via reduction of IOP by lowering aqueous humor production or by increasing outflow facility. Many of the used drugs are administrated topically direct to the eye or orally. However a relevant number of patients do not respond to the current existing glaucoma treatment options. In addition a significant number of patients face side effects like local intolerance and allergic reactions, subconjunctival hyperemia, miosis or uveitis which lead to cessation of the glaucoma therapy. Therefore the need of new and innovative therapeutic agents which control IOP is given. Since glaucoma is caused by progressive damage to the optic nerve head in particular additional neuroprotective effects in the eye would be beneficial.

Thus intense research efforts are currently ongoing for new glaucoma therapies with improved efficacy and reduced side effect profile (Lee A. J., Goldberg I., *Exp. Opin. Emer. Drugs* 2011, 16(1), 137-161; Traverso C. E. et al., *Exp. Opin. Emer. Drugs* 2011, 16(2), 293-307; Fogagnolo P., Rossetti L., *Exp. Opin. Investig. Drugs* 2011, 20(7), 947-959).

Adenosine, a purine nucleoside, is an ubiquitous modulator of numerous physiological activities which is mediated by specific cell surface receptors. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

The first identified biological action of adenosine was the effect on heart rate, atrioventricular conduction and blood pressure (Drugy A. et al., *J. Physiol.* 1929, 68, 213-237). Since then it has been reported that adenosine is involved in many physiological processes and that these effects are mainly mediated by four known subtypes of adenosine receptors—referred to as A1, A2a, A2b and A3—each of which has a unique pharmacological profile, tissue distribution and effector coupling (Jacobsen K. A. et al., *Exp. Opin. Emer. Drugs* 2007, 12, 479-492). According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors. In the case of A1 agonists (coupling preferably via $G_1$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

The development of many subtype specific adenosine receptor agonists or antagonists have been described and tested in clinical trials for many different diseases e.g. cardiac arrhythmias, neuropathic pain, myocardial perfusion imaging, inflammatory diseases and colon cancer (Jacobsen K. A. et al., Nature Rev. Drug Disc. 2006, 5, 247-264; Müller C. E. et al., Exp. Opin. Emer. Drugs 2003, 8, 537-57).

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation.

The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations.

For the adenosine A1 receptor several subtype specific agonists have been reported like NNC-21-0126, GR79236, selodenoson and capadenoson which have been reported to be in clinical development (Jacobsen K. A., *Handbook Exp. Pharmacol.*, 2009, 193, 1-24). Also the effect of adenosine A1 receptor agonists on intraocular pressure has been intensively studied and characterized. It was shown that two relatively selective adenosine A1 agonists N6-cyclohexyl-adenosine (CHA) and R(−)-N6-(2-phenylisopropyl)adenosine (R-PIA) lower intraocular pressure in rabbits (Crosson C. E., *Curr. Eye Res.* 1995, 11, 453-458; Crosson C. E. et al. *J. Ocul. Pharmacol.* 1994, 10, 379-383; Crosson C. E., *J. Pharmacol. Exp. Ther.* 1995, 273, 320-326) and cynomolgus monkeys (Kaufman P. L. et al., *Exp. Eye Res.* 1997, 64, 979-989). However the use of adenosine A1 agonists as therapeutic drugs for glaucoma or ocular hypertension is significantly limited by the effects on hemodynamic parameters as it is known that adenosine A1 agonists are crucially involved in heart rate and blood pressure regulation (Zablocki J. et al., *Handbook Exp. Pharmacol.*, 2009, 193, 25-58).

Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient [P. Ettmayer et al., *J. Med. Chem.* 47, 2393 (2004)]. In order to achieve an optimal profile of effects it is necessary in this connection for the design of the prodrug residue as well as the desired mechanism of liberation to be coordinated very accurately with the individual active ingredient, the indication, the site of action and the administration route. A large number of medicaments is administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985. A review of prodrug derivatives based on carboxylic acid esters and possible properties of such compounds can be found, for example, in K. Beaumont et al., *Curr. Drug Metab.* 4, 461-485 (2003). Also known are dipeptide prodrugs of acyclovir for treating ocular herpes infections (B. S. Anand et al., *Curr. Eye Res.* 26, No. 3-4, 151-163 (2003)) which interact with the oligopeptide transporter on the cornea, thus increasing the bioavailability of acylovir in the eye.

WO 2008/130520 claims alkinyl-substituted purine derivatives as therapeutic agent for glaucoma or ocular hypertension. WO 2010/127210 describes Adenosine derivatives like INO-8875 for reducing intraocular pressure in humans.

Substituted 3,5-dicyano-4-phenylpyridines and their prodrugs as potent and selective adenosine A1 agonists are disclosed in WO 03/53441, WO 2009/015776, WO 2009/015811, WO 2009/015812, WO 2010/072314, WO 2010/072315 and WO 2010/086101.

The object of the present invention is to provide an effective therapeutic agent for the use in the treatment and/or prophylaxis of glaucoma and/or ocular hypertension without showing the above mentioned side effects.

Surprisingly, it has now been found that the dicyanopyridines of formula (I) lower intraocular pressure after topical application to the eye without effecting hemodynamics and are thus suitable for the production of medicaments for the use in the treatment and/or prophylaxis of glaucoma and ocular hypertension.

The present invention relates to compounds of formula (I)

(I)

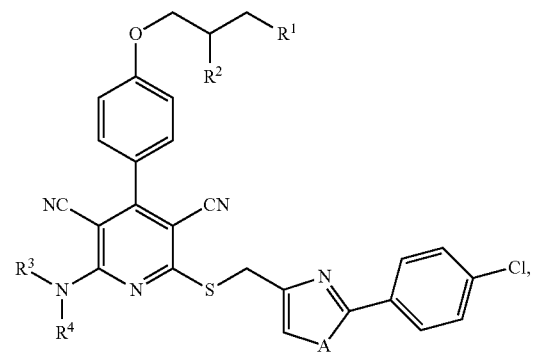

in which
A is oxygen or sulfur,
$R^1$ is hydrogen or a group of the formula

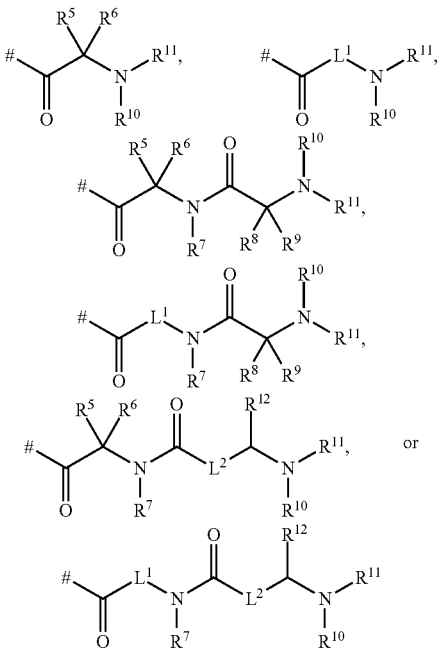

in which
\# is the attachment to the oxygen-atom,
$L^1$ is linear $(C_2-C_4)$-alkanediyl,
$L^2$ is linear $(C_1-C_3)$-alkanediyl, $R^5$ and $R^8$ are identical or different and independently selected from the group consisting of hydrogen or a side group of a natural α-amino acid or its homologues or isomers, $R^6$ and $R^9$ are independently selected from hydrogen or methyl, $R^7$ is hydrogen or $(C_1-C_4)$-alkyl, or $R^7$ and $R^8$ form together with the atoms which they are attached to a pyrrolidine- or piperidine-ring, $R^{10}$ and $R^{11}$ are identical or different and are independently selected from hydrogen
wherein $(C_1-C_4)$-alkyl may be substituted with one group selected from hydroxy, $(C_1-C_4)$-alkoxy, amino, mono-$(C_1-C_4)$-alkylamino or di-$(C_1-C_4)$-alkylamino, or $R^{10}$ and $R^8$ form together with the atoms which they are attached to a pyrrolidine- or piperidine-ring,
and $R^{12}$ is hydrogen or hydroxycarbonyl, $R^2$ is hydrogen or a group of the formula —$CH_2OR^1$,
wherein $R^1$ is defined as above, $R^3$ is hydrogen, methyl or ethyl, $R^4$ is hydrogen, methyl or ethyl, or $R^3$ and $R^4$ form together with the nitrogen-atom, which they are bound to, a azetidine-, pyrrolidine- or piperidine-ring, wherein the azetidine-, pyrrolidine- or piperidine-ring may be substituted with one or 2 substituents independently selected from the group fluoro, trifluoromethyl, methyl, ethyl, methoxy and ethoxy, and its salts, solvates and solvates of the salts, for the use in a method for the treatment and/or prophylaxis of glaucoma, normotensive glaucoma, ocular hypertension and/or combinations thereof.

In a preferred embodiment the present invention relates to compounds of formula (I), in which A is sulfur, $R^1$ is a group of the formula

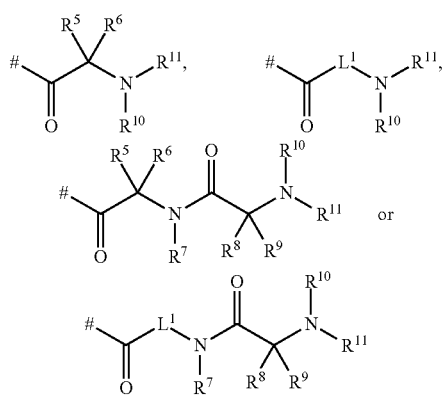

in which # is the attachment to the oxygen-atom, $L^1$ is ethane-1,2-diyl, $R^5$ is hydrogen, methyl, propane-2-yl, 1-methylpropane-1-yl, 2-methylpropane-1-yl, hydroxymethyl or 1-hydroxymethyl, $R^6$ is hydrogen, $R^7$ is hydrogen, $R^8$ is hydrogen, methyl, propan-2-yl, 1-methylpropan-1-yl, 2-methylpropan-1-yl, imidazol-4-ylmethyl, hydroxymethyl, hydroxyethyl, 2-carboxyethyl, 4-aminobutan-1-yl or 2-aminoethyl, $R^9$ is hydrogen, $R^{10}$ is hydrogen, $R^{11}$ is hydrogen, or $R^{10}$ and $R^8$ form together with the atoms which they are attached to a pyrrolidine-ring, $R^2$ is hydrogen, $R^3$ is hydrogen, $R^4$ is hydrogen, or $R^3$ and $R^4$ form together with the nitrogen-atom, which they are bound to, a azetidine-, pyrrolidine- or piperidine-ring, and its salts, solvates and solvates of the salts, for the use in a method for the treatment and/or prophylaxis of glaucoma, normotensive glaucoma, ocular hypertension and/or combinations thereof.

In a preferred embodiment the present invention also relates to compounds of formula (I), in which A is sulfur, $R^1$ is hydrogen $R^2$ is hydrogen, $R^3$ is hydrogen, $R^4$ is hydrogen, or $R^3$ and $R^4$ form together with the nitrogen-atom, which they are bound to, a azetidine-, pyrrolidine- or piperidine-ring, and its salts, solvates and solvates of the salts, for the use in a method treatment and/or prophylaxis of glaucoma, normotensive glaucoma, ocular hypertension and/or combinations thereof.

In a preferred embodiment the present invention also relates to compounds of formula (I), in which A is oxygen, $R^1$ is hydrogen $R^2$ is hydrogen or —$CH_2OH$, $R^3$ is hydrogen, $R^4$ is hydrogen, and its salts, solvates and solvates of the salts, for the use in a method for the treatment and/or prophylaxis of glaucoma, normotensive glaucoma, ocular hypertension and/or combinations thereof.

In a preferred embodiment the present invention also relates to compounds of formula (I), in which A is sulfur, $R^1$ is a group of the formula

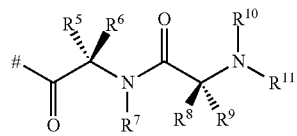

in which # is the attachment to the oxygen-atom, $R^5$ is hydrogen, methyl, propan-2-yl, 2-methylpropan-1-yl, benzyl, hydroxymethyl or 1-hydroxyethyl, $R^6$ is hydrogen, $R^7$ is hydrogen, $R^8$ is hydrogen, methyl, propan-2-yl, 1-methylpropan-1-yl, 2-methylpropan-1-yl, imidazol-4-ylmethyl, 4-aminobutan-1-yl, 2-aminoethyl, 3-aminopropan-1-yl, aminomethyl or 3-guanidinopropan-1-yl, $R^9$ is hydrogen, $R^{10}$ is hydrogen,
$R^{11}$ is hydrogen,
$R^2$ is hydrogen,
$R^3$ is hydrogen,
$R^4$ is hydrogen,
and its salts, solvates and solvates of the salts,
for the use in a method for the treatment and/or prophylaxis of glaucoma, normotensive glaucoma, ocular hypertension and/or combinations thereof.

In a preferred embodiment the present invention relates to a compound of the formula (I) selected from:
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-alaninate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-arginyl-D-alaninate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-valinate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-arginyl-D-valinate-Trihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-phenylalaninate-Dihydrochloride,
2-{4-[2-(Azetidin-1-yl)-6-({[2-(4-chlorophenyl)-1,3-thiazol-4-yl]methyl}sulfanyl)-3,5-dicyanopyridin-4-yl]phenoxy}ethyl-beta-alaninate-Trifluoroacetate,
2-{4-[2-(Azetidin-1-yl)-6-({[2-(4-chlorophenyl)-1,3-thiazol-4-yl]methyl}sulfanyl)-3,5-dicyanopyridin-4-yl]phenoxy}ethyl-L-ornithinate-Bis(trifluoroacetate),
2-{4-[2-(Azetidin-1-yl)-6-({[2-(4-chlorophenyl)-1,3-thiazol-4-yl]methyl}sulfanyl)-3,5-dicyanopyridin-4-yl]phenoxy}ethyl-L-lysyl-L-alaninate-Bis(trifluoroacetate),
2-{4-[2-({[2-(4-Chlorophenyl)-1,3-thiazol-4-yl]methyl}sulfanyl)-3,5-dicyano-6-(pyrrolidin-1-yl)pyridin-4-yl]phenoxy}ethyl-L-alanyl-L-alaninate-Hydrochloride,
2-{4-[2-({[2-(4-Chlorophenyl)-1,3-thiazol-4-yl]methyl}sulfanyl)-3,5-dicyano-6-(pyrrolidin-1-yl)pyridin-4-yl]phenoxy}ethyl-L-isoleucyl-L-alaninate-Hydrochloride,
2-{4-[2-({[2-(4-Chlorophenyl)-1,3-thiazol-4-yl]methyl}sulfanyl)-3,5-dicyano-6-(pyrrolidin-1-yl)pyridin-4-yl]phenoxy}ethyl-glycyl-L-leucinate-Hydrochloride,
(2S)-3-{4-[2-Amino-6-({[2-(4-chlorophenyl)-1,3-oxazol-4-yl]methyl}sulfanyl)-3,5-dicyanopyridin-4-yl]phenoxy}propan-1,2-diyl-(2S,2'S)-bis(2-{[(2S)-2-aminopropanoyl]amino}propanoate)-Dihydrochloride
and their salts, solvates and solvates of the salts for the use in a method for the treatment and/or prophylaxis of glaucoma, normotensive glaucoma, ocular hypertension and/or combinations thereof.

In a preferred embodiment the present invention relates to a compound of the formula (I) selected from:
2-Amino-6-({[2-(4-chlorophenyl)-1,3-thiazol-4-yl]methyl}sulfanyl)-4-[4-(2-hydroxyethoxy)phenyl]pyridine-3,5-dicarbonitrile
2-({[2-(4-Chlorophenyl)-1,3-thiazol-4-yl]methyl}sulfanyl)-4-[4-(2-hydroxyethoxy)phenyl]-6-(pyrrolidin-1-yl)pyridine-3,5-dicarbonitrile
2-({[2-(4-Chlorophenyl)-1,3-thiazol-4-yl]methyl}sulfanyl)-4-[4-(2-hydroxyethoxy)phenyl]-6-(azetidin-1-yl)pyridine-3,5-dicarbonitrile
2-Amino-6-({[2-(4-chlorophenyl)-1,3-oxazol-4-yl]methyl}sulfanyl)-4-(4-{[(2R)-2,3-dihydroxy-propyl]oxy}phenyl)pyridin-3,5-dicarbonitrile
and its salts, solvates and solvates of the salts,
and their salts, solvates and solvates of the salts for the use in a method for the treatment and/or prophylaxis of glaucoma, normotensive glaucoma, ocular hypertension and/or combinations thereof.

In a preferred embodiment the present invention relates to a compound of the formula (I) selected from:
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-alaninate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-valinate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-arginyl-D-valinate-Trihydrochloride,
and their salts, solvates and solvates of the salts for the use in a method for the treatment and/or prophylaxis of glaucoma, normotensive glaucoma, ocular hypertension and/or combinations thereof.

In a preferred embodiment the present invention also relates to compounds of formula (I), in which
$R^3$ is hydrogen,
$R^4$ is hydrogen,
and its salts, solvates and solvates of the salts,
for the use in a method for the treatment and/or prophylaxis of glaucoma, normotensive glaucoma, ocular hypertension and/or combinations thereof.

In a preferred embodiment the present invention also relates to compounds of formula (I), in which
$R^3$ and $R^4$ form together with the nitrogen-atom, which they are bound to, a azetidine-pyrrolidine- or piperidine-ring,
and its salts, solvates and solvates of the salts,
for the use in a method for the treatment and/or prophylaxis of glaucoma, normotensive glaucoma, ocular hypertension and/or combinations thereof.

The compounds of formula (I), their production and their action as potent and selective adenosine A1 agonists are disclosed in WO 03/53441, WO 2009/015776, WO 2009/015811, WO 2009/015812, WO 2010/072314, WO 2010/072315 and WO 2010/086101 respectively. The compounds mentioned in WO 03/53441, WO 2009/015776, WO 2009/015811, WO 2009/015812, WO 2010/072314, WO 2010/072315 and WO 2010/086101 in general and especially the compounds specifically are an explicit part of the description of the present invention and are hereby incorporated by reference.

Depending on the substitution pattern, the compounds of the formula (I) can exist in stereoisomeric forms, which behave either as image and mirror image (enantiomers) or which do not behave as image and mirror image (diastereomers). The invention relates both to the use of the enantiomers or diastereomers and to their respective mixtures. Just like the diastereomers, the racemic forms can be separated into the stereoisomerically uniform constituents in a known manner. Equally, the present invention also relates to the use of the other tautomers of the compounds of the formula (I) and their salts.

Salts of the compounds of the formula (I) can be physiologically acceptable salts of the substances according to the invention with mineral acids, carboxylic acids or sulfonic acids. Particularly preferred salts are, for example, those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, trifluoroacetic acid, acetic acid, propionic acid, lactic acid, tartaric acid, citric acid, fumaric acid, maleic acid or benzoic acid.

The compounds of the present invention appear preferably as hydrochlorides or trifluoroacetates.

Salts which can be mentioned are also salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethyl-amine, triethylamine, ethyldiisopropylamine, procaine, dibenzylamine, N-methylmorpholine, dihydroabietylamine, 1-ephenamine or methylpiperidine.

Hydrates or solvates are designated according to the invention as those forms of the compounds of the formula (I) which in the solid or liquid state form a molecular compound or a complex by hydration with water or coordination with solvent molecules. Examples of hydrates are sesqui-hydrates, monohydrates, dihydrates or trihydrates. Equally, the hydrates or solvates of salts of the compounds according to the invention are also suitable.

In the context of the present invention, the substituents, unless stated otherwise, have the following meaning:

Alkyl is in the context of the invention a straight-chain or branched alkyl radical having 1 to 4 carbon atoms. The following radicals may be mentioned by way of example and by way of preference: methyl, ethyl, n-propyl, isopropyl, n-butyl, isobutyl, sec-butyl and tert-butyl.

Alkanediyl is in the context of the invention a straight-chain or branched divalent alkyl radical having 1 to 4 carbon atoms. Examples which may be preferably mentioned are: ethane-1,2-diyl(1,2-ethylene), ethane-1,1-diyl, propane-1,3-diyl(1,3-propylene), propane-1,1-diyl, propane-1,2-diyl, propane-2,2-diyl, butane-1,4-diyl(1,4-butylene), butane-1,2-diyl, butane-1,3-diyl, butane-2,3-diyl.

Alkoxy is in the context of the invention a straight-chain or branched alkoxy radical having 1 to 4 carbon atoms. The following radicals may be mentioned by way of example and by way of preference: methoxy, ethoxy, n-propoxy, isopropoxy, n-butoxy and tert-butoxy.

Mono- or di-($C_1$-$C_4$)-alkylamino is in the context of the invention an amino group having one or having two identical or different straight-chain or branched alkyl substituents, which in each case contain 1 to 4 carbon atoms. For example, the following may be mentioned: methylamino, ethyl-amino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

The side group of an α-amino acid in the meaning of $R^3$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: methyl (alanine), propan-2-yl (valine), propan-1-yl (norvaline), 2-methylpropan-1-yl (leucine), 1-methylpropan-1-yl (isoleucine), butan-1-yl (norleucine), tert-butyl(2-tert-butylglycine), phenyl(2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 2-aminoethyl (2,4-diaminobutyric acid), aminomethyl (2,3-diaminopropionic acid), 3-guanidinopropan-1-yl (arginine), 3-ureidopropan-1-yl (citrulline). Preferred α-amino acid side groups in the meaning of $R^3$ are methyl (alanine), propan-2-yl (valine), 2-methylpropan-1-yl (leucine), benzyl (phenylalanine), imidazol-4-ylmethyl (histidine), hydroxymethyl (serine), 1-hydroxyethyl (threonine), 4-aminobutan-1-yl (lysine), 3-aminopropan-1-yl (ornithine), 2-aminoethyl (2,4-diaminobutyric acid), aminomethyl (2,3-diaminopropionic acid), 3-guanidinopropan-1-yl (arginine). The L configuration is preferred in each case.

The term effective amount as used herein refers to an amount of a compound of formula (I) that is effective for treatment and/or prophylaxis glaucoma, normotensive glaucoma, ocular hypertension and/or combinations thereof.

The present invention relates to selective adenosine A1 agonists, in particular the dicyanopyridines of formula (I), for the use in a method for the treatment and/or prophylaxis of glaucoma, normotensive glaucoma, ocular hypertension and/or combinations thereof.

The compounds of formula (I) act as selective adenosine A1 agonists and show a beneficial profile when administered topically to the eye, and are thus useful as an effective therapeutic agent for the treatment and/or prophylaxis of glaucoma and/or ocular hypertension.

The compounds of the present invention lower intraocular pressure when administered topically to the eye without effecting hemodynamic parameters as demonstrated in section B. Experimental methods.

The present invention relates to compounds of formula (I) for the use in a method for the treatment and/or prophylaxis of glaucoma and/or ocular hypertension.

Furthermore the present invention relates to compounds of formula (I) for the use in a method for the treatment and/or prophylaxis of high IOP resulting from traumatic hyphema, orbital edema, postoperative visco-elastic retention, intraocular inflammation, corticosteroid use, pupillary block, or idiopathic causes.

In addition the compounds of formula (I) are useful for the treatment and/or prophylaxis of various ocular hypertensive conditions, such as post-surgical and post-laser trabeculectomy ocular hypertensive episodes and as presurgical adjuncts.

The present invention further relates to a method of treating glaucoma, or other disease or disorder of the eye related to elevated intraocular pressure.

The present invention further relates to the use of compounds of formula (I) for the manufacture of medicaments for the treatment and/or prophylaxis of glaucoma and/or ocular hypertension.

A further subject of the present invention is a pharmaceutical composition comprising a compound of the formula (I).

A further subject of the present invention is a medicament, comprising a compound of the formula (I) as defined in any of claims 1 to 4 in combination with one or more further active ingredients selected from the group consisting of alpha adrenergic agonist, beta blocker and carbonic anhydrase inhibitor.

A further subject of the present invention is the use of a combination of one or more compounds of the formula (I) with one or more other active compounds in a method for the treatment and/or prophylaxis of glaucoma, high IOP resulting from traumatic hyphema, orbital edema, postoperative visco-elastic retention, intraocular inflammation, corticosteroid use, pupillary block, or idiopathic causes. Examples of suitable combination active ingredients may for example and preferably be mentioned:

alpha adrenergic agonist such as for example alphagan; iopidin, isoglaucon, catapres, aruclonin beta blocker such as for example timolol, timoptol, optimal, carteolol, ocupress, betoptic, betagan carbonic anhydrase inhibitor such as for example dorzolamide, trusopt, diamox, Acetazolamid, brinzolamid, dorzolamid, dichlorphenamid, methazolamid.

Further disclosed herein is a method for the treatment and/or prophylaxis of high IOP, including glaucoma, ocular hypertension, normotensive glaucoma or a combination thereof comprising administering an effective amount of at least one compound of formula (I) or of a medicament comprising at least one compound of formula (I) in combination with an inert, non-toxic, pharmaceutically suitable excipient to the eye.

Further disclosed herein is a method for the treatment and/or prophylaxis of high IOP, including glaucoma, ocular hypertension, normotensive glaucoma or a combination thereof comprising administering an effective amount of at least one compound of formula (I) or of a medicament comprising at least one compound of formula (I) in combination with an inert, non-toxic, pharmaceutically suitable excipient to the eye and at least one further active compound selected from the group consisting of alpha adrenergic agonists, beta blockers and carbonic anhydrase inhibitors.

Preferred administration route is topical administration to the eye.

Topical preparations of the invention include solutions, sprays, lotions, gels, creams, powders, powder sprays, pastes, emulsions, foams and sticks which comprise the active ingredient of the formula (I), where appropriate also a plurality of active ingredients.

Suitable pharmaceutically-acceptable carriers for topical application include those suited for use in lotions, creams, gels, solutions, ointments, viscous solutions, eye drops, emulsions, gel-forming solutions and the like.

The topically applicable preparations of the invention comprise 0.1 to 99%, preferably 0.5 to 20% by weight of active ingredient of the formula (I).

Ointments comprise hydrocarbon gels, lipogels, absorption bases, W/O ointment bases, mixed emulsions or polyethylene glycols as base.

Gels comprise solvents such as water, ethanol, isopropanol or propylene glycol and are produced using gel formers such as cellulose ethers, alginates, polyacrylates, bentonite, gelatin, tragacanth, polyvinylpyrrolidone or polyvinyl alcohol. Lipophilic gel bases or microemulsions can also be used.

Advantageously, the composition is sterile and can be in dosage unit form, e.g., suitable for topical ocular use. The composition can be packaged in a form suitable for metered application, such as in container equipped with a dropper.

In a preferred embodiment, the composition is a solution prepared using a physiological saline solution as a carrier. The pH of the solution is, preferably, maintained between 4.5 and 8.0 using an appropriate buffer system. A neutral pH is more preferred. Compositions of the invention can also comprise pharmaceutically acceptable preservatives, stabilizers and/or surfactants.

For this purpose, the active compounds can be converted into the customary preparations in a manner known per se. This takes place using inert, nontoxic, pharmaceutically suitable carriers, excipients, solvents, vehicles, emulsifiers and/or dispersants.

Suitable excipients which may be mentioned are, for example: water, nontoxic organic solvents such as, for example, paraffins, vegetable oils (e.g. sesame oil), alcohols (e.g. ethanol, glycerol), glycols (e.g. polyethylene glycol), solid carriers such as natural or synthetic ground minerals (e.g. talc or silicates), sugars (e.g. lactose), emulsifiers, dispersants (e.g. polyvinylpyrrolidone) and glidants (e.g. magnesium sulfate).

Further disclosed herein is an ophthalmic composition comprising a compound of formula (I) and a pharmaceutically acceptable vehicle or excipient.

BRIEF DESCRIPTION OF THE DRAWINGS

FIG. 1A: A graph showing IOP as mmHg in unconscious rats after topical administration of 10 mg/ml of the compound of Example 1, 10 mg/ml $N^6$-cyclopentyladenosine, and control FIG. 1B: A graph showing IOP as percent of zero value in unconscious rats after topical administration of 10 mg/ml of the compound of Example 1, 10 mg/ml $N^6$-cyclopentyladenosine, and control.

FIG. 2: A graph of IOP as percent of zero value in unconscious rats, after topical administration of 10 mg/ml of the compound of Example 9 and control.

FIG. 3: A graph of blood pressure in conscious rats after topical administration of 10 mg/ml of the compound of Example 1 and $N^6$-cyclopentyladenosine.

FIG. 4: A graph of blood pressure in conscious rats after topical administration of 10 mg/ml of the compound of Example 9 and control.

FIG. 5: A graph of IOP in conscious rabbits after topical administration of INO-8875 and control.

FIG. 6: A graph of IOP in conscious rabbits after topical administration of the compound of Example 1 and control.

FIG. 7: A graph showing the effect on mean arterial pressure of conscious rabbits after topical administration of INO-8875.

FIG. 8: A graph of blood pressure in conscious rabbits after topical administration of the compound of Example 1.

EXAMPLES

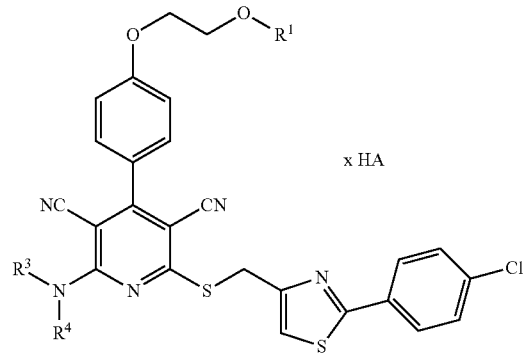

TABLE 1

| Example | R¹ | R³ | R⁴ | HA |
|---|---|---|---|---|
| 1 | H₃C-CH(NH-)-C(=O)-NH-CH(CH₂CH₂CH₂CH₂NH₂)- (Ala-Lys) | H | H | 2 HCl |
| 2 | (CH₃)₂CH-CH(NH-)-C(=O)-NH-CH(CH₂CH₂CH₂CH₂NH₂)- (Val-Lys) | H | H | 2 HCl |
| 3 | H₃C-CH(NH-)-C(=O)-NH-CH(CH₂CH₂CH₂NHC(=NH)NH₂)- (Ala-Arg) | H | H | 2 HCl |
| 4 | (CH₃)₂CH-CH(NH-)-C(=O)-NH-CH(CH₂CH₂CH₂NHC(=NH)NH₂)- (Val-Arg) | H | H | 3 HCl |
| 5 | PhCH₂-CH(NH-)-C(=O)-NH-CH(CH₂CH₂CH₂CH₂NH₂)- (Phe-Lys) | H | H | 2 HCl |

The synthesis of examples 1 to 5 and corresponding starting materials is described in WO 2009/015811 in detail.

TABLE 2

| Example | R¹ | —NR³R⁴ | HA |
|---|---|---|---|
| 6 | #–C(=O)–CH₂CH₂–NH₂ (β-Ala) | azetidin-1-yl | CF₃CO₂H |
| 7 | #–C(=O)–CH(NH₂)–CH₂CH₂CH₂–NH₂ (Orn) | azetidin-1-yl | CF₃CO₂H |
| 8 | H₃C-CH(NH-)-C(=O)-NH-CH(CH₂CH₂CH₂CH₂NH₂)- (Ala-Lys) | azetidin-1-yl | CF₃CO₂H |
| 9 | H₃C-CH(NH-)-C(=O)-NH-CH(CH₃)- (Ala-Ala) | pyrrolidin-1-yl | HCl |
| 10 | H₃C-CH(NH-)-C(=O)-NH-CH(CH(CH₃)CH₂CH₃)- (Ala-Ile) | pyrrolidin-1-yl | HCl |
| 11 | (CH₃)₂CHCH₂-CH(NH-)-C(=O)-NH-CH(CH₃)- (Leu-Ala) | pyrrolidin-1-yl | HCl |

\* is the attachment to the dicyanopyridine

Example 12

2-Amino-6-({[2-(4-chlorophenyl)-1,3-thiazol-4-yl]methyl}sulfanyl)-4-[4-(2-hydroxyethoxy)phenyl]pyridine-3,5-dicarbonitrile

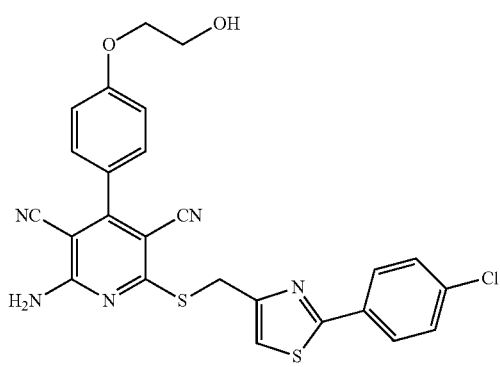 [SMILES: N#Cc1c(N)nc(SCc2csc(-c3ccc(Cl)cc3)n2)c(C#N)c1-c1ccc(OCCO)cc1]

The synthesis of example 12 is described in WO 03/53441 (example 6) in detail.

Example 13

2-({[2-(4-Chlorophenyl)-1,3-thiazol-4-yl]methyl}sulfanyl)-4-[4-(2-hydroxyethoxy)phenyl]-6-(pyrrolidin-1-yl)pyridine-3,5-dicarbonitrile

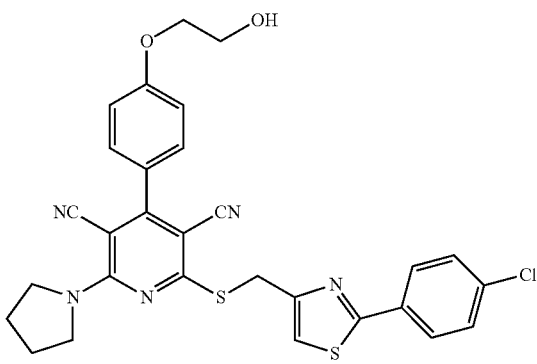 [SMILES: N#Cc1c(SCc2csc(-c3ccc(Cl)cc3)n2)nc(N2CCCC2)c(C#N)c1-c1ccc(OCCO)cc1]

The synthesis of example 13 is described in WO 2010/086101 (example 1) in detail.

Example 14

2-({[2-(4-Chlorophenyl)-1,3-thiazol-4-yl]methyl}sulfanyl)-4-[4-(2-hydroxyethoxy)phenyl]-6-(azetidin-1-yl)pyridine-3,5-dicarbonitrile

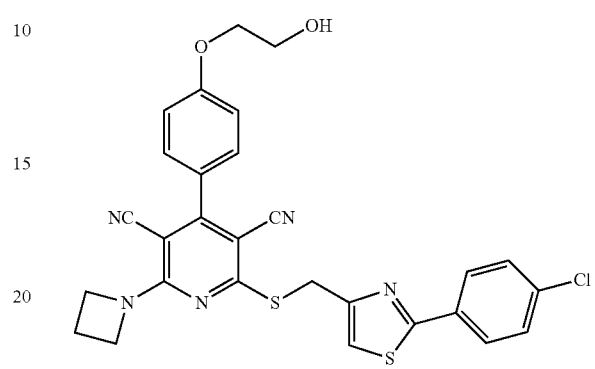

The synthesis of example 14 is described in WO 2010/086101 (example 49) in detail.

Example 15

2-Amino-6-({[2-(4-chlorophenyl)-1,3-oxazol-4-yl]methyl}sulfanyl)-4-(4-{[(2R)-2,3-dihydroxy-propyl]oxy}phenyl)pyridin-3,5-dicarbonitrile

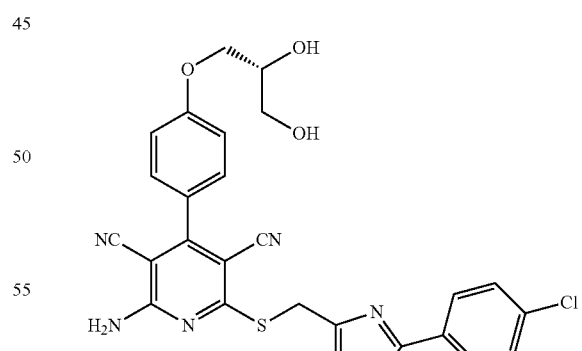

The synthesis of example 15 is described in WO 2009/015776 (example 8A) in detail.

Example 16

(2S)-3-{4-[2-Amino-6-({[2-(4-chlorophenyl)-1,3-oxazol-4-yl]methyl}sulfanyl)-3,5-dicyanopyridin-4-yl]phenoxy}propan-1,2-diyl-(2S,2'S)-bis(2-{[(2S)-2-aminopropanoyl]amino}propanoate)-Dihydrochloride

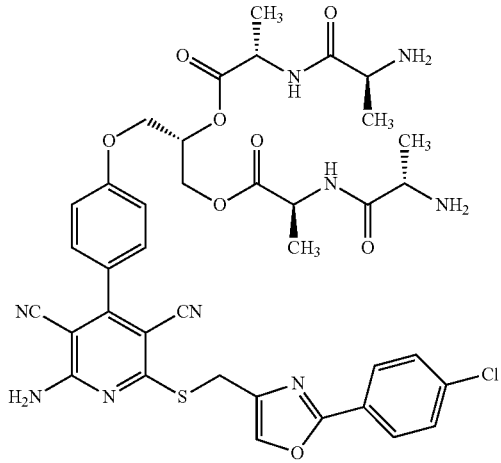 [SMILES: C[C@H](N)C(=O)N[C@@H](C)C(=O)OC[C@H](COc1ccc(-c2c(C#N)c(N)nc(SCc3coc(-c4ccc(Cl)cc4)n3)c2C#N)cc1)OC(=O)[C@H](C)NC(=O)[C@H](C)N]

The synthesis of example 16 is described in WO 2010/072314 (example 33) in detail.

B. Experimental Methods

Advantageous pharmacological properties of the compounds of the present invention can be determined by the following methods.

The abbreviations are used in the following experiments:

IOP intraocular pressure

SEM (standard error of mean)

PBS (phosphate buffered saline)

In each experiment the control animals received the corresponding solvent.

B-1. IOP Measurements in Rats

Wistar rats with a body weight of about 300 g were anesthetized with isoflurane (2-3% in $O_2:N_2O=1:2$). The compounds were dissolved/suspended in an aqueous solution of sodium chloride (0.9%) and administered topically to the eye in 10 μl volume at a concentration of 10 mg/ml. IOP was measured with a rebound tonometer (TonoLab) at different time points after application of the compounds. Ocular pressure and effects of hemodynamic parameters can be monitored in this model. $N^6$-Cyclopentyl-Adenosine (CPA) is a known adenosine A1 agonist having the structure shown below:

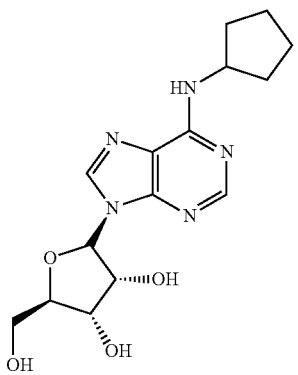

FIG. 1A shows IOP (as mm Hg) over time after topical administration of control, $N^6$-Cyclopentyl-Adenosine (CPA) and Example 1 at a dose of 10 mg/ml.

FIG. 1B shows IOP (as percent of zero value) over time after topical administration of control, $N^6$-Cyclopentyl-Adenosine (CPA) and Example 9 at a dose of 10 mg/ml.

Table 3 gives IOP (as percent of zero value) after topical administration of $N^6$-Cyclopentyl-Adenosine (CPA) and Example 1 at a dose of 10 mg/ml at time points from 0 min to 120 min

TABLE 3

| compound | Time [min] | IOP [%] | ±SEM |
|---|---|---|---|
| Control | 0 | 100.0 | 0.0 |
| Control | 15 | 89.6 | 3.7 |
| Control | 30 | 92.3 | 4.8 |
| Control | 45 | 88.6 | 2.9 |
| Control | 60 | 93.4 | 5.1 |
| Control | 90 | 95.7 | 4.4 |
| Control | 120 | 96.3 | 4.3 |
| Example 1 | 0 | 100.0 | 0.0 |
| Example 1 | 15 | 93.6 | 5.7 |
| Example 1 | 30 | 80.6 | 2.6 |
| Example 1 | 45 | 77.7 | 3.0 |
| Example 1 | 60 | 70.0 | 1.7 |
| Example 1 | 90 | 75.9 | 5.9 |
| Example 1 | 120 | 76.6 | 3.5 |
| CPA | 0 | 100.0 | 0.0 |
| CPA | 15 | 65.0 | 3.3 |
| CPA | 30 | 58.5 | 3.5 |
| CPA | 45 | 46.3 | 4.9 |
| CPA | 60 | 42.5 | 3.6 |
| CPA | 90 | 44.8 | 2.3 |
| CPA | 120 | 59.0 | 2.0 |
| Example 4 | 0 | 100.0 | 0.0 |
| Example 4 | 30 | 73.8 | 6.1 |
| Example 4 | 60 | 80.0 | 7.9 |
| Example 4 | 90 | 76.0 | 7.7 |
| Example 2 | 0 | 100.0 | 0.0 |
| Example 2 | 30 | 95.3 | 9.9 |
| Example 2 | 60 | 73.3 | 3.9 |
| Example 2 | 90 | 73.8 | 6.6 |

FIG. 2 shows IOP (as percent of zero value) over time after topical administration of control and Example 9 at a dose of 10 mg/ml.

Table 4 gives IOP (as percent of zero value) after topical administration of Example 9 and control at a dose of 10 mg/ml at time points from 0 min to 120 min

TABLE 4

| compound | Time [min] | IOP [%] | ±SEM |
|---|---|---|---|
| Control | 0 | 100.0 | 0.0 |
| Control | 15 | 96.7 | 3.8 |
| Control | 30 | 106.9 | 6.4 |
| Control | 60 | 104.4 | 6.1 |
| Control | 90 | 97.7 | 5.5 |
| Control | 120 | 101.7 | 6.5 |
| Example 9 | 0 | 100.0 | 0.0 |

TABLE 4-continued

| compound | Time [min] | IOP [%] | ±SEM |
|---|---|---|---|
| Example 9 | 15 | 81.6 | 3.1 |
| Example 9 | 30 | 84.4 | 2.4 |
| Example 9 | 60 | 83.7 | 4.0 |
| Example 9 | 90 | 85.3 | 2.4 |
| Example 9 | 120 | 83.7 | 3.9 |

B-2. Blood Pressure Measurement in Telemetric Rats

Normotensive wistar rats with a body weight of 300 to 350 g were used for this experimental study. Blood pressure was monitored in freely moving conscious animals by radiotelemetry. Briefly, the telemetric system (DSI Data Science International, MN, USA) is composed on 3 basic elements: implantable transmitters (TA11PA-C40), receivers (RA1010) and a computer-based acquisition software (Dataquest A.R.T 2.1 for Windows). Rats were instrumented with pressure implants for chronic use at least 14 days prior the experiments. Rats were anesthetized with isoflurane (2-3% in $O_2:N_2O=1:2$). During catheter implantation under anesthesia, rats were kept on a heating mat. A fluid-filled sensor catheter was inserted upstream into the exposed descending aorta between the iliac bifurcation and the renal arteries. According to the DSI guidelines the tip of the telemetric catheter was located just caudal to the renal arteries and secured by tissue adhesive. The transmitter body was affixed to the inner peritoneal wall before closure of abdomen. In a hardware configuration equipped for 24 animals, each rat cage was positioned on top of an individual receiver platform. After activation of the implanted transmitters, A.R.T., an on-line data acqusition system, samples data and converts telemetric pressure signals into mm Hg. The compounds were dissolved/suspended in an aqueous solution of sodium chloride (0.9%) and administered topically to the eye in 10 μl volume at a concentration of 10 mg/ml. Given are % deviations from the control run-in period of 2 hours before substance administration.

FIG. 3 shows effects on mean arterial blood pressure after topical administration of control, $N^6$-Cyclopentyl-Adenosine and Example 1 at a dose of 10 mg/ml over time.

Table 5 gives mean arterial pressure (MAP) as percent change of zero value after topical administration of control, $N^6$-Cyclopentyl-Adenosine and Example 1 at different time points from −0.25 h to 6.25 h.

TABLE 5

| Time [hours] | control MAP | ±SEM | CPA MAP | ±SEM | Example 1 MAP | ±SEM | Example 4 MAP | ±SEM | Example 2 MAP | ±SEM |
|---|---|---|---|---|---|---|---|---|---|---|
| −0.25 | 0.0 | 0.0 | 0.0 | 0.0 | 0.0 | 0.0 | 0.0 | 0.0 | 0.0 | 0.0 |
| 0.25 | 4.5 | 1.8 | −25.4 | 2.8 | 1.2 | 1.3 | 7.3 | 1.5 | 10.7 | 3.3 |
| 0.75 | 0.1 | 1.1 | −71.3 | 5.0 | −6.1 | 0.8 | 1.0 | 2.3 | 1.6 | 2.6 |
| 1.25 | −4.7 | 2.0 | −58.9 | 7.7 | −6.0 | 0.5 | −2.0 | 1.5 | 0.3 | 2.0 |
| 1.75 | −1.2 | 3.4 | −42.6 | 7.1 | −2.5 | 1.2 | −0.8 | 2.0 | −0.2 | 1.8 |
| 2.25 | 4.2 | 3.3 | −30.3 | 5.5 | −2.5 | 1.6 | 0.7 | 2.6 | −1.1 | 1.6 |
| 2.75 | −3.4 | 0.8 | −17.6 | 6.1 | −1.5 | 2.3 | 0.6 | 2.2 | 1.9 | 2.7 |
| 3.25 | −2.3 | 1.8 | −16.4 | 5.5 | −1.4 | 3.2 | 0.1 | 2.5 | 2.0 | 2.3 |
| 3.75 | −4.9 | 1.1 | −9.0 | 3.1 | −1.6 | 3.5 | 1.0 | 2.9 | −2.2 | 1.5 |
| 4.25 | −3.4 | 1.1 | −8.4 | 2.9 | −1.5 | 4.1 | −1.5 | 1.6 | −0.9 | 1.2 |
| 4.75 | −2.0 | 1.2 | −5.3 | 3.6 | −1.7 | 3.7 | −0.3 | 1.8 | −0.8 | 1.7 |
| 5.25 | −3.3 | 0.9 | −0.7 | 4.4 | −6.0 | 4.4 | −1.7 | 2.3 | −3.1 | 1.4 |
| 5.75 | 4.5 | 1.7 | −2.9 | 2.2 | −3.8 | 4.6 | −3.8 | 2.2 | −4.2 | 1.8 |
| 6.25 | −4.6 | 1.1 | −2.7 | 3.2 | −6.0 | 3.7 | −3.6 | 1.6 | −4.0 | 1.6 |

FIG. 4 shows effects on mean arterial blood pressure after topical administration of control and Example 9 at a dose of 10 mg/ml over time.

Table 6 gives mean arterial pressure (MAP) as percent change of zero value after topical administration of control and Example 9 at different time points from −0.25 h to 6.25 h.

TABLE 6

| Time [hours] | Control MAP | ±SEM | Example 9 MAP | ±SEM |
|---|---|---|---|---|
| −0.25 | 0.00 | 0.0 | 0.00 | 0.0 |
| 0.25 | 10.26 | 2.1 | 7.05 | 1.3 |
| 0.75 | 0.04 | 1.1 | 0.94 | 1.8 |
| 1.25 | −1.16 | 1.6 | −3.02 | 1.9 |
| 1.75 | 0.74 | 1.0 | −2.50 | 1.0 |
| 2.25 | −0.27 | 1.0 | 0.37 | 1.3 |
| 2.75 | 0.62 | 1.8 | −0.95 | 1.6 |
| 3.25 | 3.67 | 2.3 | −1.51 | 1.0 |
| 3.75 | 1.38 | 2.6 | 0.08 | 1.1 |
| 4.25 | −1.52 | 1.0 | −1.54 | 1.5 |
| 4.75 | 0.46 | 1.0 | −1.99 | 1.9 |
| 5.25 | −1.68 | 1.2 | −0.43 | 1.6 |
| 5.75 | −1.37 | 1.8 | −0.04 | 1.9 |
| 6.25 | −1.03 | 2.2 | −2.42 | 1.9 |

B-3. Nerve Crush Model

Mice (all at least 7 weeks old) are deeply anesthetized, and optic nerves are intraorbitally crushed. After treating the mice for two weeks with compounds, i.e. the adenosine A1 agonists they are sacrificed and eyes are withdrawn. Flatmounts of the retinas are prepared. The degenerated retinal ganglion cells are analyzed and counted in the different treatment groups.

B-4. Retinal Ischemia Model

Male Lewis rats weighing 200 to 250 g and male C57BL/6J mice weighing 25 to 30 g are anesthetized. The anterior chamber of one eye is cannulated with a needle attached to a line infusing normal saline to increase intraocular pressure.

IOP is measured by a handheld tonometer (TonoLab) in rat eyes for the next up to 120 minutes. The other eye of the same animal is set up as a control. After ischemia, the needle is withdrawn, IOP is normalized, and reflow of the retinal circulation is documented visually. Animals are killed at different times after I/R injury.

B-5. IOP Measurements in Conscious Rabbits

Female New Zealand rabbits with a body weight of about 4-5 kg were used to measure inner eye pressure (IOP). The compounds were dissolved/suspended in a solution of 10% transcutol, 10% solutol and 80% PBS, and given by topical administration at the eye in 30 µl volume. IOP was measured with a rebound tonometer (TonoVet) at different time points after application of the drugs. INO-8875 is a known adenosine A1 agonist having the structure shown below:

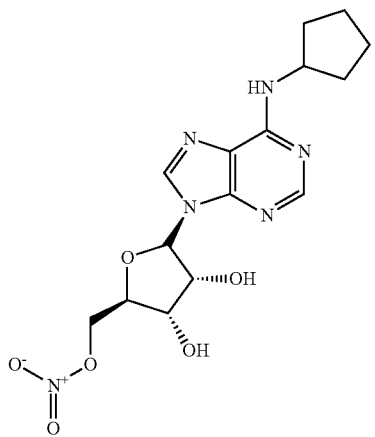

FIG. 5 shows IOP as percent of zero value in rabbits of INO-8875 at dosages of 1.0, 3.0 and 10.0 mg/mL after topical administration.

Table 7 gives IOP as percent of zero value in rabbits of INO-8875 at dosages of 1.0, 3.0 and 10.0 mg/mL after topical administration.

TABLE 7

| time | INO-8875 (1.0 mg/mL) | | INO-8875 (3.0 mg/mL) | | INO-8875 (10.0 mg/mL) | | control | |
|---|---|---|---|---|---|---|---|---|
| [min] | IOP | ±SEM | IOP | ±SEM | IOP | ±SEM | IOP | ±SEM |
| 0 | 100.0 | 0.0 | 100.0 | 0.0 | 100.0 | 0.0 | 100.0 | 0.0 |
| 30 | 85.3 | 5.0 | 89.3 | 3.7 | 74.0 | 3.6 | 105.0 | 4.7 |
| 60 | 86.7 | 5.5 | 81.3 | 1.3 | 60.0 | 2.6 | 99.0 | 4.0 |
| 90 | 93.3 | 5.8 | 79.0 | 1.5 | 61.3 | 3.0 | 99.3 | 5.8 |
| 120 | 100 | 8.9 | 87.3 | 7.4 | 65.0 | 4.6 | 99.0 | 1.0 |

FIG. 6 shows IOP as percent of zero value in rabbits of Example 1 at dosages of 3.0 and 10.0 mg/mL after topical administration.

Table 8 gives IOP as percent of zero value in rabbits of Example 1 at dosages of 3.0 and 10.0 mg/mL after topical administration.

TABLE 8

| time | Example 1 (3.0 mg/mL) | | Example 1 (10.0 mg/mL) | | control | |
|---|---|---|---|---|---|---|
| [min] | IOP | ±SEM | IOP | ±SEM | IOP | ±SEM |
| 0 | 100.0 | 0.0 | 100.0 | 0.0 | 100.0 | 0.0 |
| 30 | 82.7 | 4.3 | 79.8 | 7.0 | 104.6 | 3.4 |
| 60 | 76.7 | 3.1 | 66.2 | 4.8 | 90.6 | 3-9 |
| 90 | 82.1 | 3.6 | 71.3 | 5.1 | 98.0 | 5.2 |
| 120 | 81.9 | 3.0 | 68.5 | 4.8 | 92.2 | 4.0 |

B-6. Assessment of Blood Pressure and Heart Rate in Telemetric Rabbits

Implantation of Telemetric Senders in Female New Zealand Rabbits:

New Zealand rabbits were used for implantation of the telemetric senders. Rabbits were pre-anaesthetized with Rompun® and Ketavet® i.m. at a dose of 5 mg/kg (in 0.25 ml/kg)+40 mg/kg (in 0.40 ml/kg) respectively. Anaesthesia was maintained with an i.v. infusion of Rompun® and Ketavet® (5-15 ml/h) with a solution of Rompun 2 ml (20 mg/1 ml)+Ketavet 4 ml (100 mg/ml) and 60 ml 0.9% aqueous solution of sodium chloride. Before surgery the hairs at the inner side of the back leg were completely removed and the skin were treated with local anaesthetic Xylocaln® Spray and disinfected with Braunol®. The rabbits were transferred to a sterile surgery unit and covered with sterile swabs and compressions. The skin was opened and the arteria femoralis was carefully dissected free and the pressure catheter of the telemetric implant C50 PXT® (DSI/Data Science International, St. Paul, Minn., U.S.A.) was inserted in the vein and forwarded abdominally under control of the pressure signal. The signal was detected with the RMC1-DSI® receiver plates and visualized with the PONEMAH® physiology platform software DSI/Data Science International, St. Paul, Minn., U.S.A.). After detection of a stable blood pressure signal the catheter was fixed with tissue-glue "Gewebepad" (DSI) and the two ECG electrodes were cut close to the transmitter. The transmitter was fixed under the skin of the rabbit. The wound was closed and finally treated with Nebacetin® Powder Spray. Post-operative analgesia was done with Metamizol i.m. 50 mg/kg in 0.1 ml/kg for 5 days after surgery. In addition a 5 day antibiotic therapy with Terramycin®/LA 20 mg/kg with 0.1 ml/kg was applied i.m. All rabbits recovered fully within one week of the surgery and were after 2 weeks adjustment to the measurement procedure used for the blood pressure detection.

Registration of MAP and HR in Conscious Female New Zealand Rabbits:

The rabbits with telemetric implants were housed for 5 hours in a transportation box which was placed on the RMC1-DSI® receiver plates. The signals were visualized, compiled and analyzed with the PONEMAH® physiology platform software. The systolic (SAP), diastolic (DAP) and mean arterial blood pressure (MAP) levels were registered in mmHg and the heart rate (HR) in beat/minutes was calculated from the interval between the systoles. Baseline levels for SAP, DAP and MAP as for HR were registered over a 2 hour equilibration period. The compounds were dissolved/suspended in a solution of 10% transcutol, 10% solutol and 80% PBS, and given by topical administration at the eye in 30 µl volume. Controls received the corresponding solvents. Baseline levels for SAP, DAP and MAP as for HR were registered over a 3 hour period after application.

FIG. 7 shows effects of INO-8875 at dosages of 1.0, 3.0 and 10.0 mg/mL on mean arterial blood pressure after topical administration.

Table 9 gives mean arterial pressure (MAP) as mm Hg of INO-8875 at dosages of 1.0, 3.0 and 10.0 mg/mL after topical administration.

TABLE 9

| Time [min] | INO-8875 (1.0 mg/mL) MAP [mm Hg] | ±SEM | INO-8875 (3.0 mg/mL) MAP [mm Hg] | ±SEM | INO-8875 (10.0 mg/mL) MAP [mm Hg] | ±SEM | control MAP [mm Hg] | ±SEM |
|---|---|---|---|---|---|---|---|---|
| 0 | 123.9 | 12.1 | 118.5 | 13.2 | 114.5 | 7.3 | 113.6 | 9.4 |
| 30 | 111.3 | 13.3 | 101.8 | 17.7 | 89.5 | 11.4 | 114.2 | 13.2 |
| 60 | 110.9 | 13.6 | 104.9 | 17.8 | 86.9 | 10.5 | 113.8 | 13.4 |
| 90 | 112.6 | 13.3 | 105.7 | 17.1 | 90.3 | 8.9 | 114.8 | 10.3 |
| 120 | 106.0 | 14.5 | 109.0 | 20.4 | 90.0 | 40.0 | 108.3 | 18.2 |

FIG. 8 shows effects of Example 1 at dosages of 3.0 and 10.0 mg/ml on mean arterial blood pressure after topical administration.

Table 10 gives mean arterial pressure (MAP) as mm Hg of Example 1 at dosages of 3.0 and 10.0 mg/mL after topical administration.

TABLE 10

| Time [min] | Example 1 (3.0 mg/mL) MAP | ±SEM | Example 1 (10.0 mg/mL) MAP | ±SEM | control MAP | ±SEM |
|---|---|---|---|---|---|---|
| 0 | 117.1 | 28.6 | 115.9 | 10.7 | 113.6 | 9.4 |
| 30 | 114.5 | 29.4 | 118.8 | 15.0 | 114.2 | 13.2 |
| 60 | 110.4 | 28.7 | 112.0 | 14.2 | 113.8 | 13.4 |
| 90 | 117.8 | 34.0 | 112.8 | 14.1 | 114.8 | 10.3 |
| 120 | 106-7 | 31.6 | 105.4 | 17.9 | 108.3 | 18.2 |

The invention claimed is:

1. A method of treatment of glaucoma, normotensive glaucoma, ocular hypertension and/or combinations thereof comprising administering a therapeutically effective amount of a compound of formula (I) to a human or animal in need thereof, wherein the compound of formula (I) is:

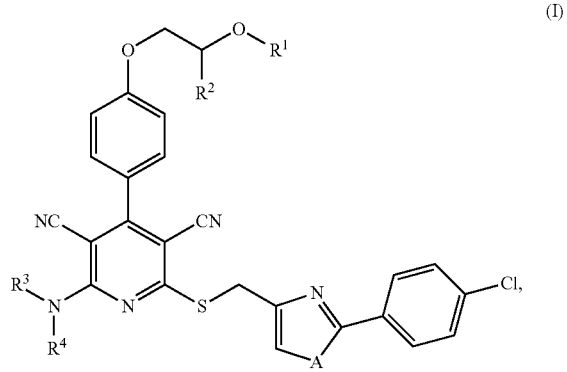

in which
A is oxygen or sulfur,
$R^1$ is hydrogen or a group of the formula

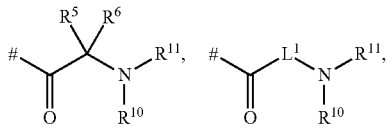

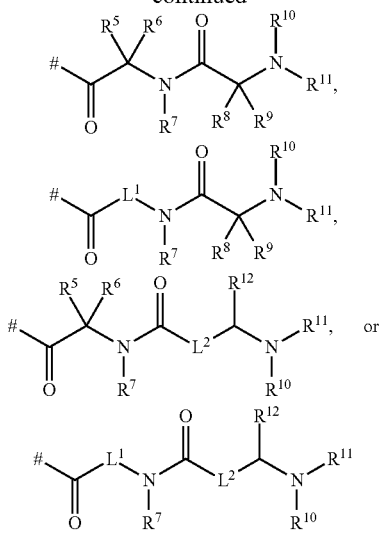

in which
# is the attachment to the oxygen-atom,
$L^1$ is linear $(C_2$-$C_4)$-alkanediyl,
$L^2$ is linear $(C_1$-$C_3)$-alkanediyl,
$R^5$ and $R^8$ are identical or different and independently selected from the group consisting of hydrogen or a side group of a natural α-amino acid or its homologues or isomers,
$R^6$ and $R^9$ are independently selected from hydrogen or methyl,
$R^7$ is hydrogen or $(C_1$-$C_4)$-alkyl,
or
$R^7$ and $R^5$ form together with the atoms which they are attached to a pyrrolidine- or piperidine-ring,
$R^{10}$ and $R^{11}$ are identical or different and are independently selected from hydrogen or $(C_1$-$C_4)$-alkyl,
wherein $(C_1$-$C_4)$-alkyl may be substituted with one group selected from hydroxy, $(C_1$-$C_4)$-alkoxy, amino, mono-$(C_1$-$C_4)$-alkylamino or di-$(C_1$-$C_4)$-alkylamino,
or
$R^{10}$ and $R^8$ form together with the atoms which they are attached to a pyrrolidine- or piperidine-ring,
and
$R^{12}$ is hydrogen or hydroxycarbonyl,
$R^2$ is hydrogen or a group of the formula —$CH_2OR^1$,
wherein $R^1$ is defined as above,
$R^3$ is hydrogen, methyl or ethyl,
$R^4$ is hydrogen, methyl or ethyl,
or
$R^3$ and $R^4$ form together with the nitrogen-atom, which they are bound to, a azetidine-, pyrrolidine- or piperidine-ring,
wherein the azetidine-, pyrrolidine- or piperidine-ring may be substituted with one or 2 substituents independently selected from the group fluoro, trifluoromethyl, methyl, ethyl, methoxy and ethoxy,
or a salt thereof.

2. The method of claim 1, wherein in the compound of formula (I)

A is sulfur,
R¹ is a group of the formula

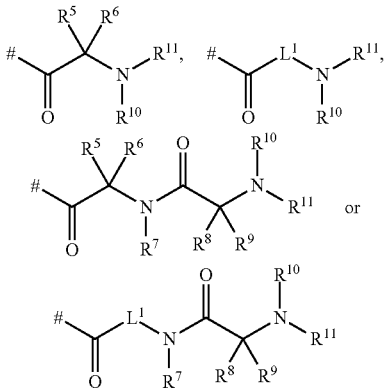

in which
# is the attachment to the oxygen-atom,
L¹ is ethane-1,2-diyl,
R⁵ is hydrogen, methyl, propane-2-yl, 1-methylpropane-1-yl, 2-methylpropane-1-yl, hydroxymethyl or 1-hydroxymethyl,
R⁶ is hydrogen,
R⁷ is hydrogen,
R⁸ is hydrogen, methyl, propan-2-yl, 1-methylpropan-1-yl, 2-methylpropan-1-yl, imidazol-4-ylmethyl, hydroxymethyl, hydroxyethyl, 2-carboxyethyl, 4-aminobutan-1-yl or 2-aminoethyl,
R⁹ is hydrogen,
R¹⁰ is hydrogen,
R¹¹ is hydrogen,
or
R¹⁰ and R⁸ form together with the atoms which they are attached to a pyrrolidine-ring,
R² is hydrogen
R³ is hydrogen,
R⁴ is hydrogen,
or
R³ and R⁴ form together with the nitrogen-atom, which they are bound to, a azetidine-pyrrolidine- or piperidine-ring,
or a salt thereof.

3. The method of claim 1, wherein in the compound of formula (I)
A is sulfur,
R¹ is a group of the formula

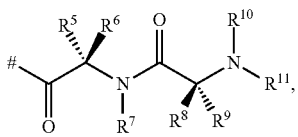

in which
# is the attachment to the oxygen-atom,
R⁵ is hydrogen, methyl, propan-2-yl, 2-methylpropan-1-yl, benzyl, hydroxymethyl or 1-hydroxyethyl,
R⁶ is hydrogen,
R⁷ is hydrogen,
R⁸ is hydrogen, methyl, propan-2-yl, 1-methylpropan-1-yl, 2-methylpropan-1-yl, imidazol-4-ylmethyl, 4-aminobutan-1-yl, 2-aminoethyl, 3-aminopropan-1-yl, aminomethyl or 3-guanidinopropan-1-yl,
R⁹ is hydrogen,
R¹⁰ is hydrogen,
R¹¹ is hydrogen,
R² is hydrogen,
R³ is hydrogen,
R⁴ is hydrogen,
or a salt thereof.

4. The method of claim 1, wherein the compound of formula (I) is selected from:
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-alaninate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-arginyl-D-alaninate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-valinate-Dihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-arginyl-D-valinate-Trihydrochloride,
2-{4-[2-Amino-6-({[2-(4-chlorophenyl)-1,3-thiazol-4-yl]methyl}sulfanyl)-3,5-dicyanopyridin-4-yl]phenoxy}ethyl-L-lysyl-D-phenylalaninate-Dihydrochloride,
2-{4-[2-(Azetidin-1-yl)-6-({[2-(4-chlorophenyl)-1,3-thiazol-4-yl]methyl}sulfanyl)-3,5-dicyanopyridin-4-yl]phenoxy}ethyl-beta-alaninate-Trifluoroacetate,
2-{4-[2-(Azetidin-1-yl)-6-({[2-(4-chlorophenyl)-1,3-thiazol-4-yl]methyl}sulfanyl)-3,5-dicyanopyridin-4-yl]phenoxy}ethyl-L-ornithinate-Bis(trifluoroacetate),
2-{4-[2-(Azetidin-1-yl)-6-({[2-(4-chlorophenyl)-1,3-thiazol-4-yl]methyl}sulfanyl)-3,5-dicyanopyridin-4-yl]phenoxy}ethyl-L-lysyl-L-alaninate-Bis(trifluoroacetate),
2-{4-[2-({[2-(4-Chlorophenyl)-1,3-thiazol-4-yl]methyl}sulfanyl)-3,5-dicyano-6-(pyrrolidin-1-yl)pyridin-4-yl]phenoxy}ethyl-L-alanyl-L-alaninate-Hydrochloride,
2-{4-[2-({[2-(4-Chlorophenyl)-1,3-thiazol-4-yl]methyl}sulfanyl)-3,5-dicyano-6-(pyrrolidin-1-yl)pyridin-4-yl]phenoxy}ethyl-L-isoleucyl-L-alaninate-Hydrochloride,
2-{4-[2-({[2-(4-Chlorophenyl)-1,3-thiazol-4-yl]methyl}sulfanyl)-3,5-dicyano-6-(pyrrolidin-1-yl)pyridin-4-yl]phenoxy}ethyl-glycyl-L-leucinate-Hydrochloride,
(2S)-3-{4-[2-Amino-6-({[2-(4-chlorophenyl)-1,3-oxazol-4-yl]methyl}sulfanyl)-3,5-dicyanopyridin-4-yl]phenoxy}propan-1,2-diyl-(2S,2'S)-bis(2-{[(2S)-2-aminopropanoyl]amino}propanoate)-Dihydrochloride
or a salt thereof.

5. The method of claim 1, wherein the compound is administered topically to the eye.

6. The method of claim 1, wherein the compound of formula (I) is administered in the form of an ophthalmic composition comprising the compound of formula (I) and a pharmaceutically acceptable vehicle or excipient.

7. The method of claim 6, wherein the ophthalmic composition further comprises at least one active compound selected from the group consisting of an alpha adrenergic agonist, a beta blocker, and a carbonic anhydrase inhibitors.

8. The method of claim 1, wherein the treatment is done without effecting hemodynamics.

9. The method of claim 8, wherein the treatment is done without effecting the blood pressure.
10. The method of claim 8, wherein the treatment is done without effecting heart rate.
11. The method of claim 1, wherein the compound of formula (I) is
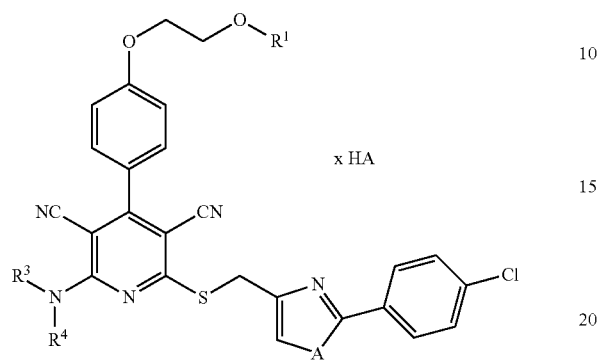
in which
R¹ is
R³ is hydrogen,
R⁴ is hydrogen and
HA is 2 HCl.
* * * * *